United States Patent
Mentink

(10) Patent No.: US 12,226,498 B2
(45) Date of Patent: *Feb. 18, 2025

(54) EMULSIFYING COMPOSITION COMPRISING A WATER-IN-OIL EMULSIFIER AND A CYCLODEXTRIN OF SELECTED PARTICLE SIZE, CAPABLE OF PROVIDING AN OIL-IN-WATER EMULSION WITH IMPROVED SENSORY EFFECTS FOR COSMETIC USE

(71) Applicant: ROQUETTE FRERES, Lestrem (FR)

(72) Inventor: Léon Mentink, Lille (FR)

(73) Assignee: Roquette Freres, Lestrem (FR)

( * ) Notice: Subject to any disclaimer, the term of this patent is extended or adjusted under 35 U.S.C. 154(b) by 771 days.

This patent is subject to a terminal disclaimer.

(21) Appl. No.: 17/309,551

(22) PCT Filed: Dec. 4, 2019

(86) PCT No.: PCT/FR2019/052928
§ 371 (c)(1),
(2) Date: Jun. 4, 2021

(87) PCT Pub. No.: WO2020/115436
PCT Pub. Date: Jun. 11, 2020

(65) Prior Publication Data
US 2022/0023162 A1   Jan. 27, 2022

(30) Foreign Application Priority Data
Dec. 5, 2018 (FR) ........................... 1872344

(51) Int. Cl.
*A61K 8/06* (2006.01)
*A61K 8/73* (2006.01)

(52) U.S. Cl.
CPC .............. *A61K 8/062* (2013.01); *A61K 8/738* (2013.01); *A61K 2800/412* (2013.01)

(58) Field of Classification Search
CPC ... A61K 8/062; A61K 8/738; A61K 2800/412
See application file for complete search history.

(56) References Cited

U.S. PATENT DOCUMENTS

| | | | |
|---|---|---|---|
| 5,714,445 A | 2/1998 | Trinh et al. | |
| 6,428,796 B1 | 8/2002 | Gers-Barlag et al. | |
| 2013/0011454 A1 | 1/2013 | Park et al. | |
| 2016/0051459 A1* | 2/2016 | Perassinoto | A61K 8/062 424/59 |
| 2017/0319441 A1* | 11/2017 | Goutsis | A61K 8/19 |
| 2018/0263866 A1* | 9/2018 | Deckner | A61P 17/16 |

FOREIGN PATENT DOCUMENTS

| | | | |
|---|---|---|---|
| CN | 105832568 A | 8/2016 | |
| EP | 0685227 A1 | 12/1995 | |
| EP | 2091502 B1 | 12/2013 | |
| FR | 2858777 A1 | 2/2005 | |
| FR | 1762841 A1 | 6/2019 | |
| JP | S5858139 A | 4/1983 | |
| JP | 2001131056 A | 5/2001 | |
| JP | 2011006641 A | 1/2011 | |
| WO | WO-2008003685 A1 * | 1/2008 | ............ A61K 8/062 |
| WO | 2018105747 A1 | 4/2018 | |

OTHER PUBLICATIONS

English translation of WO2008003685 (A1) from EPO. (Year: 2024).*
Paar, "Particle size distribution," downloaded Jun. 1, 2024 from https://wiki.anton-paar.com/us-en/particle-size-distribution/ (Year: 2021).*
Nageen Arora, et al., "Latest Technology Advances in Cosmaceuticals", International Journal of Pharmaceutical Sciences and Drug Research, Jul. 1, 2012 (Jul. 1, 2012), pp. 16 8-182, abstract; left column; p. 177.
The Australian Examination Report, mailed on Jul. 26, 2024, in the related Australian Appl. No. 2019393137.
Aussie Soap Supplies, "Rice Bran Oil," retrieved from the Internet URL: https://aussiesoapsupplies.com.au/rice-bran-oil/, published on Aug. 31, 2014.

* cited by examiner

*Primary Examiner* — Michael P Cohen

(57) ABSTRACT

The present invention relates to a sensory emulsifying composition, in particular for cosmetic use, capable of obtaining a liquid oil-in-water-type emulsion comprising at least one cyclodextrin in the form of solid particles, said particles having a volumetric average particle size d(4,3), measured by laser granulometry, of between 2 and 20 µm, preferably between 3 and 12 µm, and more preferably between 4 and 8 µm, and at least one emulsifier of natural origin selected from water-in-oil emulsifiers, having a hydrophilic-lipophilic balance (HLB) of less than 8.

20 Claims, No Drawings

EMULSIFYING COMPOSITION COMPRISING A WATER-IN-OIL EMULSIFIER AND A CYCLODEXTRIN OF SELECTED PARTICLE SIZE, CAPABLE OF PROVIDING AN OIL-IN-WATER EMULSION WITH IMPROVED SENSORY EFFECTS FOR COSMETIC USE

The present invention relates to an emulsifying composition of plant origin, ready for use and directly for cold use with applications in particular in the cosmetics sector. This composition comprises at least one cyclodextrin in the form of solid particles, said particles having a volumetric average particle size d(4.3) measured by laser granulometry, of less than or equal to 20 μm, and at least one emulsifier of natural origin. The emulsifying composition according to the invention may be used as a cosmetic composition as such, or as a pre-mix in order to enable an emulsion to be carried out and stabilized. This emulsifying composition in particular enables very fine liquid oil-in-water (O/W) emulsions, with various textures compatible with skin, to be easily carried out. The obtained compositions present a soft and smooth feel, even when they present a high content in fatty phase in the emulsion, and spread easily, without pilling.

An emulsion is a dispersion of a liquid (or of a material rendered liquid) in fine droplets in another liquid that is non-miscible with the former. It presents a macroscopically homogeneous appearance but appears heterogeneous under the microscope. The liquid in droplet form is referred to as dispersed phase (or discontinuous), while the other liquid is referred to as dispersing phase (or continuous). In general, an emulsion is composed of two phases (simple emulsion): a hydrophilic phase (aqueous) and a lipophilic phase (fatty). An oil-in-water emulsion is referred to as a direct emulsion.

Emulsions are widely used in the cosmetics sector. As a cosmetic product, these emulsions must meet the needs of consumers, who simultaneously demand efficacy, safety, and pleasant sensory properties. In order to satisfy these demands, formulations of emulsions have, over time, been made more complex by integrating ever more functional or sensory ingredients of synthetic origin, generally derived from petrochemicals.

It is known that the majority of cosmetic compositions in the form of emulsion, typically simple emulsions, are stabilized by surfactants. By way of example, document EP 0 685 227 proposes a highly complex system of sunscreen cosmetic compositions, comprising an aqueous continuous phase, a protective system capable of filtering UV rays, a surfactant, organic solvents (lower alcohols and polyols) and at least one polymer or more particularly a cross-linked copolymer (alkyl acrylates, vinyl acetate). Document FR 2 858 777 in turn describes an oil-in-water emulsion containing at least one fatty product (fatty acid esters, waxes, butters, natural oils—vegetal, animal, marine origin, synthetic or mineral-, hydrogenated oils and mixtures thereof), at least one surfactant (ethoxylated polyglycerol fatty acid esters, alcohol ethoxylates), at least one co-surfactant and water.

However, the use of surfactants in products intended for application on humans or animals, whether in topical or oral form, can be problematic. Indeed, surfactants can damage cell membranes. Thus, efforts are being made, in particular in the cosmetic sector, to reduce the potentially harmful effects of surfactants.

Moreover, cosmetic products currently need to meet a new consumer expectation: natural origin, and in an even more exacting manner, the naturalness of the compositions. Indeed, consumers are now seeking cosmetic products consisting essentially of natural ingredients or ingredients of natural origin, having minimum chemical modifications or synthesis grafts or grafts of petrochemical origin.

In addition, one of the aims of the present invention is to provide a composition that enables the formation of stable emulsions, even according to a "cold" process, by dispersion in an aqueous phase and subsequent addition of oil or fatty product. Such a composition enables the elimination of the reliance on surfactants of oil origin and non-biodegradable, in particular glycol derivatives and ethoxylated derivatives. The composition according to the present invention also enables the manufacture of Pickering-type emulsions. Emulsions of this type are devoid of surfactants and are stabilized by colloidal microparticles, generally silicas, which are placed at the interfaces of the continuous phase and the dispersed phase. In the context of the present invention, these colloidal particles would be organic particles consisting of inclusion complexes between at least one cyclodextrin and at least one fatty molecule. These particles are advantageously very compatible with the skin or hair and do not damage the cell membranes.

This result is all the more remarkable since the state of the art shows that the manufacture of emulsifying compositions for cosmetic use containing cyclodextrins does not enable emulsions to be easily and directly obtained cold; it was hitherto necessary to rely on surfactants of oil origin. In particular, this is what is disclosed in document EP 2 091 502 B1 which describes an oil-in-water (O/W) emulsion containing water, a fatty substance, a modified polysaccharide, and a cyclodextrin, the essential characteristic of this O/W emulsion being that it contains surfactant agents with a molecular weight of less than 5000 g/mol and in an amount of less than 2% by weight. Thus, carrying out emulsifying systems containing cyclodextrins enabling very fine and very stable emulsions to be obtained and that, without relying on surfactants of oil origin, was not known, or evident.

Furthermore, the main appeal for a consumer for the cosmetic product lies in its sensory properties, well before the benefits can be observed. The challenge facing a cosmetic product is thus to grant a cosmetic benefit while providing, before or during application, the most pleasant sensations possible. Meanwhile, the removal of functional or sensory ingredients derived from petrochemicals, their substitution for ingredients of natural origin, or the introduction of new natural ingredients or of natural origin, can be accompanied by a deterioration of sensory properties of the cosmetic product in a more or less marked manner, in particular their appearance, product pick-up, their application or their properties once applied on the skin, or dander. Thus, the compositions meeting the naturalness criteria can prove difficult to spread, tend to pill, or feel squeaky, brittle, or even insufficiently slippery when applied. These insufficient or deteriorated sensory perceptions are detrimental to the quality or image of a cosmetic product.

A new type of emulsifying composition has been developed by the applicant, and marketed under the name "Beauté by Roquette® DS 146". This innovative emulsifying composition is the object of a patent application FR1762841 that is yet to be published. This composition is a mixture of a beta-cyclodextrin "Beauté by Roquette® CD 102" and a natural water-in-oil emulsifying agent, such as e.g. polyglyceryl-3 diisostearate, which enables the physical-chemical and sensory properties of emulsions to be optimally adjusted and adapted, and stable viscosities to be obtained. By providing emulsions, e.g. creams, very interesting and acceptable, but perfectible, sensory perceptions have been noted with this emulsifying composition of natural origin developed by the applicant. In comparison with formulations comprising petrochemical surfactants, creams comprising this emulsifying composition can, on certain skins, be harder to spread, be less penetrating, susceptible to pilling, and can present a less soft and smooth feel, and sometimes greasier.

Thus, an objective of the present invention is to provide an improved emulsifying composition, for cosmetic use, offering improved sensory properties with respect to the emulsifying composition of the application FR1762841, in particular relating to the smooth effect, ease of spreading, soft feel, squeakiness upon application, the penetration of the composition, and pilling.

Another objective of the present invention is to provide a composition of 100% natural origin. The natural origin of the ingredients used for formulating products for everyday use as cosmetic compositions is a major issue today, not only with a view to preserving and protecting our environment but also for the wellbeing of the consumers. Thus, the composition according to the present invention enables the replacement of surfactants of synthetic origin and in particular oil origin, in particular ethoxylated, which today we seek to replace for environmental reasons, due to their poor biodegradability, and safety, due to the harmfulness of ethylene oxide widely used to produce polyethoxylated surfactants, which is toxic and flammable).

Another objective of the present invention is to provide a ready-to-use composition, enabling a very simple implementation for the formulator, with a minimal energy input, in particular by the introduction of all the ingredients in the same tank or reactor (so-called one-pot formulation). From the point of view of its implementation, the emulsifying composition object of the present invention is advantageously for use according to "a cold process", i.e. even at room temperature. "Cold process" is understood as the fact that the emulsifying composition can be implemented directly by dispersion in water at a water temperature of less than 45° C., better of less than 35° C. and better still at room temperature.

Another objective of the present invention is to provide a composition for broad spectrum cosmetic use, that is multipurpose from the point of view of the contemplated final products; from this point of view, the composition according to the invention can be used in products ranging from lotions, creams, gels, milks, etc. Additionally, said composition is advantageously non-irritating and non-allergenic for the skin. It further provides the advantage that it does not depend on the pH nor the presence of electrolytes; in other words, its emulsifying capacity is not affected by the pH of the medium, nor by the presence of mono-, di- or trivalent salts. This criteria is all the more important given that, typically, products for cosmetic use and, in particular, for topical application are susceptible to being subjected or exposed to pH variations (by way of example, the pH of the skin is slightly acidic, and varies between 4 and 6). Having an emulsifying composition that does not present a particular usage limit in terms of pH thus represents a very great technical advantage for a cosmetic composition.

All of these objectives that constitute a complex technical problem to be solved, are finally achieved through the main object of the present invention, which consists of an emulsifying composition, preferably for cosmetic use, capable of obtaining a liquid oil-in-water-type emulsion comprising:
a) at least one cyclodextrin in the form of solid particles, said particles having a volumetric average particle size d(4.3), measured by laser granulometry, of between 2 and 20 µm, preferably between 3 and 12 µm, and more preferably between 4 and 8 µm,
b) and at least one emulsifier of natural origin selected from water-in-oil-type emulsifiers, having a hydrophilic-lipophilic balance of less than 8, most preferably of less than or equal to 7.

The calculation of the HLB takes into account the molecular masses of the hydrophilic parts and the molecular masses of the molecule under consideration and can be obtained according to the following equation:

$$HLB = 20 \frac{\text{Molecular mass of hydrophilic part}}{\text{Molecular mass of the molecule}} \quad \text{[Math. 1]}$$

Cyclodextrin

The composition according to the invention implements at least one cyclodextrin in the form of solid particles, said particles having a volumetric average particle size d(4.3) measured by laser granulometry, of less than or equal to 20 µm, preferably of less than or equal to 12 µm, and most preferably of less than or equal to 8 µm.

In the present application, the term "cyclodextrin" designates and includes any of the cyclodextrins known to a skilled person, such as native and non-substituted cyclodextrins containing 6 to 12 glucose units linked by covalent bonds between carbons 1 and 4, and in particular the alpha-, beta- and gamma-cyclodextrins respectively containing 6, 7 and 8 glucose units.

This term also covers "cyclodextrin derivatives", namely molecules of which a part at least of the OH-hydroxyl groups has been transformed into OR groups, where R generally designates an alkyl group. From this point of view, the cyclodextrin derivatives in particular include the methylated, ethylated cyclodextrins, but also those substituted with a hydroxyalkyl group such as hydroxypropylated and hydroxyethylated cyclodextrins.

The preferred cyclodextrins according to the present invention are the alpha-, beta- and gamma-cyclodextrins. According to a preferred embodiment, the cyclodextrin implemented in the composition according to the invention is a beta-cyclodextrin, preferably "native", that is the hydroxyl groups of which are not chemically substituted.

In particular, the cyclodextrin may be presented in the form of a crystalline, pseudo-crystalline or amorphous powder.

In the context of the present invention, the cyclodextrin is present in the form of solid particles characterized by a volumetric average particle size d(4.3) measured by laser granulometry, of less than or equal to 20 µm, preferably of less than or equal to 12 µm, and most preferably of less than or equal to 8 µm. According to a preferred embodiment, the volumetric average size of the solid cyclodextrin particles is of between 2 µm and 20 µm, preferably of between 3 µm and 12 µm, and most preferably of between 4 µm and 8 µm.

The solid cyclodextrin particles can have any geometric shape, regular or irregular, and can be well individualized cyclodextrin crystals or agglomerates of cyclodextrin crystals linked together by crystal bridges. Preferably, the solid cyclodextrin particles have regular geometric shapes.

The volumetric average size, generally denoted d(4.3), is calculated according to ISO standard 9276-2:2014 based on the volumetric particle size distributions measured by laser diffraction granulometry, e.g. using a laser particle size analyzer of the MasterSizer® range, e.g. "Mastersizer 2000™", "Mastersizer 3000™", "Mastersizer 3000E™", from the company Malvern Instruments®, or a laser particle size analyzer "Particula LA960" from the company Horiba©. These methods of measuring by laser diffraction can be implemented using a wet process or a dry process, according to the guiding principles of the ISO standard 13320:2009. When the wet process is used, it is recommended that 2-propanol be used as the measurement fluid.

Preferably, the solid cyclodextrin particles have a volumetric particle size distribution, measured by laser diffraction granulometry, the characteristic diameters d(10), d(50) and d(90) of which are:
a) the diameter d(10) is of less than or equal to 5.0 μm, preferably of less than or equal to 2.5 μm, and/or
b) the diameter d(50) is of less than or equal to 15.0 μm, preferably of less than or equal to 10.0 μm, and/or
c) the diameter d(90) is of less than or equal to 30.0 μm, preferably of less than or equal to 25.0 μm.

The characteristic diameters d(10), d(50) and d(90), as defined in the ISO standard 13320:2009 under the notations ×10, ×50 and ×90, are the particle diameters respectively corresponding to 10%, 50% and 90% of the volumetric cumulative particle size distribution.

According to a preferred embodiment, the solid cyclodextrin particles have a volumetric particle size distribution, measured by laser diffraction granulometry, the characteristic diameters d(10), d(50) and d(90) of which are:
a) the diameter d(10) is of between 0.8 and 5.0 μm, preferably of between 1.0 and 2.5 μm, and
b) the diameter d(50) is of between 5 and 15.0 μm, preferably of between 7 and 10.0 μm, and
c) the diameter d(90) is of between 15 and 30.0 μm, preferably of between 20 and 25.0 μm.

Even more preferably, the solid cyclodextrin particles have a volumetric particle size distribution, measured by laser diffraction granulometry, having a coefficient of variation of less than or equal to 100%, preferably of less than or equal to 90%, and most preferably of less than or equal to 73%. As defined in the ISO standard 13320:2009, the coefficient of variation of the particle size distribution is the standard deviation of the particle size distribution divided by the volumetric average size d(4.3), also referred to as volumetric average diameter.

According to this preferred embodiment, the cyclodextrin is thus presented in the form of solid particles the volumetric size distribution of which is measured by laser diffraction granulometry, has the following characteristics:
a) A volumetric average size d(4.3) of between 2 and 20 μm, preferably of between 3 and 12 μm, and more preferably of between 4 and 8 μm,
b) A coefficient of variation of less than or equal to 100%, preferably of less than or equal to 90%, and more preferably of less than or equal to 73%.

Thanks to this selected particular size, the cyclodextrin particles contribute to the improvement of sensory touch perceptions, in particular increasing the soft sensation. Moreover, this use enables a clear reduction in the squeaky sensation upon application, as well as a reduction in pilling, even a disappearance of this pilling depending on the nature of the skins.

Water-in-Oil Emulsifier for an Oil-in-Water Emulsion.

In the present Application, the term water-in-oil emulsifier, also referred to as O/W, "of natural origin" designates all emulsifiers derived from renewable resources, in particular extracted or secreted by plants, micro-organisms or algae and capable of obtaining, after physical, chemical or enzymatic modification, a water-in-oil-type emulsion.

The Applicant was able to observe after numerous tests and experiment designs, that in a completely surprising and unexpected manner, the linking of a cyclodextrin, of an emulsifier used for the preparation of water-in-oil-type emulsions having a hydrophilic-lipophilic balance (HLB) of less than 8, far from preventing the formation of an emulsion in the direct sense, that is of the oil-in-water type, and compromising the stability of this type of O/W emulsion, has a very favorable effect on the preparation thereof and acts as a stabilizer, by making the emulsion more stable over time and in temperature.

This is all the more surprising since the efficacy of an emulsifier is known for being above all linked to its solubility in each of the two phases. The phase in which the emulsifier is the most soluble forms the continuous phase of the emulsion. Thus, a water-soluble emulsifier preferably stabilizes an oil-in-water O/W emulsion. The emulsifying composition according to the present invention, directly usable cold to prepare O/W emulsions, presents particularly weak solubility in water, to the order of only 1.8% at 25° C. whilst beta-cyclodextrin, as a cyclodextrin, is retained according to the preferred embodiment.

Not wanting to be tied to any one theory, it seems that the presence of very weak amounts of a W/O emulsifier of natural origin greatly facilitates the in situ formation of inclusion complexes between the cyclodextrin and certain specific molecules present in the dispersed fatty phase, and this in the form of colloidal, solid or semi-liquid particles, which are placed at the oil and water interfaces. These particles are very physically and sensorially compatible with the skin or hair and do not damage the cell membranes.

In particular, the average HLB of the overall emulsifying system of said composition is of less than 8, preferably of less than or equal to 7. The average HLB of the overall emulsifying system of the composition is calculated by carrying out a weighted average of HLB of each emulsifier, by weighting the HLB of each emulsifier present by its mass fraction with respect to the total mass of the emulsifiers present.

The W/O emulsifier of natural origin having a hydrophilic/lipophilic balance (HLB) of less than 8 is preferably present in the emulsifying composition in a W/O emulsifier/cyclodextrin ratio of between 0.01:1 and 1:1, preferably of between 0.05:1 and 0.5:1, more preferably of between 0.10:1 and 0.30:15 and better still of between 0.15:1 and 0.30:1.

Preferably, the W/O emulsifier of natural origin is selected from the following products, provided they meet the condition on the HLB hereinbefore: non-ethoxylated polyol fatty esters, and in particular from glycerol, polyglycerol, sorbitol, sorbitan, anhydrohexitol non-ethoxylated fatty esters, such as in particular isosorbide, mannitol, xylitol, erythritol, maltitol, sucrose, glucose, polydextrose non-ethoxylated fatty esters, non-ethoxylated fatty esters of hydrogenated glucose syrups, dextrin non-ethoxylated fatty esters and non-ethoxylated fatty esters of hydrolyzed starches.

The W/O emulsifier of natural origin is preferably selected from being naturally biodegradable in a hydrated natural medium. In particular it can be non-ethoxylated polyol fatty esters obtained from fatty acid or by transesterification from oil or oil mixtures. The fatty acids used comprise 8 to 22 carbon atoms, preferably 10 to 18 carbon atoms, and in particular 12 to 18 carbon atoms. These acids can be linear or branched, saturated or unsaturated, have one or several side hydroxyl groups. The oils can be saturated or unsaturated, from liquid to solid at room temperature, and optionally have hydroxyl groups, preferably with an iodine value of between 1 and 145, and in particular of 5 to 105.

The W/O emulsifier of natural origin can also be selected from naturally biodegradable products in a hydrated natural medium, in particular with a hydrophilic-lipophilic balance (HLB) of between 1.5 and 6.0, preferably of between 2.0 and 5.0, and better still of between 3.0 and 5.0.

The W/O emulsifier of natural origin can, in particular, be selected from glycerol fatty esters, and in particular from oleates, stearates, glycerol isostearates such as e.g. the following products: glyceryl laurate (preferably presenting a HLB of 5.2), glyceryl oleate (preferably having a HLB of 4) such as IMWITOR 948, glyceryl isostearate Schercemol GMIS (preferably having a HLB of 3.5) of Lubrizol Schercemol and glyceryl monostearate (preferably having a HLB of 3.5) of Sympatens-GMS.

It can also be selected from sorbitan or sorbitol fatty esters, in particular from laurates, palmitate, oleates, stearate, sorbitan isostearates such as e.g. the products sorbitan trioleate Kosteran-O/3 (preferably presenting a HLB of 1.8); sorbitan oleate MONTANE 80 VG or SPAN 80-LQ-(RB) or Kosteran-O/1 (preferably having a HLB of 4.3); sorbitan isostearate Kosteran-I/1 (preferably having a HLB of 4.3), sorbitan stearate Kosteran-S/1 (preferably having a HLB of 4.7); sorbitan monopalmitate (preferably having a HLB of 6.6).

It can also be selected from sucrose fatty esters such as, e.g. sucrose distearate SP60-C of Sisterna, sucrose polystearate SP10-C of Sisterna, saccharose cocoate (preferably having a HLB of 6).

The W/O emulsifier of natural origin can in particular be selected from polyglycerol esters and preferably from esters derived from the reaction of polyglycerols comprising from 2 to 12 glycerol units, preferably from 3 to 6 glycerol units, with at least one partially hydrogenated or non-hydrogenated vegetable oil with an iodine value of between 1 and 1 5, and in particular of 5 to 10. It may particularly be polyglycerol oleic, stearic, isostearic and ricinoleic esters and in particular the following products: polyglyceryl-4 isostearate preferably having a HLB of 3 (such as HYDRIOL® PGI of HYDRIOR), polyglyceryl-10 pentaoleate preferably having a HLB 3.5 (such as DECAGLYN 5-OV), polyglyceryl-6 polyricinoleate (such as HEXAGLYN PR-15), polyglyceryl-2 sesquiisostearate preferably having a HLB~4 (such as Hostcerin DGI of Clariant and Dermofeel® GO soft of Evonik Dr. Straetmans), polyglyceryl-3 ricinoleate preferably having a HLB of 3.5, polyglyceryl-3 polyricinoleate preferably having a HLB of 4 (such as IMWITOR 600), polyglyceryl-3 polyricinoleate preferably having a HLB-4 (such as Dermofeel® PGPR of Evonik Dr. Straetmans GmbH), polyglyceryl-2 sesquioleate preferably having a HLB of 4 (such as Dermofeel® GO soft of Evonik Dr. Straetmans GmbH), polyglyceryl-2 diisostearate (such as Emulpharma® PG20 of Res Pharma), polyglyceryl-3 diisostearate preferably having a HLB of 5.5 (such as Plurol® Diisostearique CG of Gattefossé, Lameform® TGI of BASF, IMWITOR® PG3 DIS of 101 Oleo GmbH, Cithrol™ PG32IS of Croda, DUB ISO G3 of Stéarinerie Dubois, Polyaldo® 3-1-S of Lonza, Jolee 7245 of Oléon and MASSOCARE PG3D of Masso), polyglyceryl-3 oleate preferably having a HLB of 6.2 (such as I-MUL PGO 31 of Ivanhoe Industries), polyglyceryl-3 monostearate preferably having a HLB of 7.2, polyglyceryl-2 dipolyhydroxystearate (such as Dehymuls PGPH of Cognis), polyglyceryl-2 diisostearate (such as Emulpharma PG20 of Respharma), polyglyceryl-3 cocoate (such as Emulpharma® Ecotech of Res Pharma).

A more preferred ester is that derived from the reaction of polyglycerol-3 and isostearic acid (INCI name: polyglyceryl-3 diisostearate) preferably having a HLB equal to 5.5.

The W/O emulsion of natural origin can consist of fatty ester mixtures, in particular polyglycerol fatty esters, sorbitan fatty esters or glucose esters such as in particular mixtures such as the products Nikkomulse WO-NS of Nikko Chemicals (Polyglyceryl-6 polyricinoleate, polyglyceryl-2 isostearate, disteardimonium hectorite), Tego Care LTP of Evonik (sorbitan laurate, polyglyceryl-4 laurate, dilauryl citrate), Sympatens-W/4500 (sorbitan oleate, polyglyceryl-3 polyricinoleate), Sympatens-O/2500 G (sorbitan stearate, methylglucose sesquistearate), Symbio®muls WO of Dr. Straetmans (polyglyceryl-3 polyricinoleate, sorbitan sesquioleate, cetyl ricinoleate, glyceryl caprate, cera alba, magnesium stearate, aluminum stearate), Ecomuls 2 in 1 of Natura-Tec (glyceryl oleate, polyglyceryl-3-polyricinoleate, *Olea europaea* (olive) oil unsaponifiables), HIPEgel *Olea* of Alchemy (glycerin, isopropyl palmitate, water, sucrose stearate, sucrose laurate).

Effects of Selecting the Particle Size of Cyclodextrin

Comparatively to an emulsifying composition comprising a cyclodextrin with a volumetric average size greater than or equal to 90 µm, such the emulsifying composition "Beauté by Roquette® DS 146" marketed by Roquette Frères, the emulsifying composition according to the invention enables emulsions that are easier to spread to be obtained, having a smoother and softer feel, a significantly lower squeakiness, penetrating faster on keratinous materials, and leading to no or little pilling. Optionally, the emulsifying composition according to the invention also enables interesting sensory effects to be obtained, such as a particular texture or a sensation of freshness, according to the proportions used.

The interesting properties of said emulsifying composition result from the combination of two compounds used that have a good synergy, both in terms of emulsion stability of and sensory properties. While very satisfactory results are obtained regardless of the proportions in which these compounds are associated, particularly convincing results are obtained when they are linked in very precise ratio.

In particular, each of the different constituents of the emulsifying composition according to the invention can be integrated into a different phase of the final emulsion, before proceeding to the emulsification. Alternatively, the different compounds of the present composition according to the invention are mixed with each other to constitute a premix, said premix being able to be added to any one of these phases of the emulsion in which the pre-mix will be used. The invention advantageously enables these two embodiments with the same compounds, which enables increased flexibility and a simplified use. For information purposes, the applicant markets an emulsifying composition in the form of a pre-mix outside the scope of the invention of the present application, under the name of "Beauté by Roquette® DS 146", containing a beta-cyclodextrin "Beauté by Roquette® CD 102" with a volumetric average size, measured by laser granulometry using a dry process, equal to about 95 µm.

The emulsifying composition according to the invention in particular presents the advantage of being completely of natural origin, and of being used according to a "cold" process (that is implementation at room temperature. Said composition according to the invention is, in particular, for cosmetic use and, thus, is not sensitive to weak pH or salinity variations of the medium, is not an irritant and is not susceptible to cause allergies, in particular skin allergies. Additionally, the composition according to the invention can be used to carry out all types of emulsion, in particular Pickering-type emulsions, and is thus appropriate for a wide variety of uses: creams, milks, serums, lotions, etc.

Water

The emulsifying composition can contain water in the form of so-called "combined or bound" water and/or in the form of so-called "free" water. The combined or bound water consists of water molecules included in the crystalline structures of the cyclodextrin and/or polyol powders, and water molecules absorbed at the surface of these powders by physical hydration equilibrium. The free water consists of water molecules that can freely circulate between the cyclodextrin and/or polyol powders. In particular, this free water can put the cyclodextrin and/or polyol powders in suspension.

According to an embodiment, the emulsifying composition comprises a combined or bound water content of between 1% and 25%, by weight with regard to the total weight of said emulsifying composition. Preferably, the combined or bound water content is between 2% and 15%, most preferably between 3% and 10%.

According to an embodiment, the emulsifying composition comprises a free water content of less than or equal to 50% by weight with regard to the total weight of said emulsifying composition. Preferably this free water content is of less than or equal to 40%, more preferably at 30%, and most preferably at 20%.

Polyol

According to an embodiment, the emulsifying composition likewise comprises at least one polyol.

The polyols referred to in the present Applicant are all the known polyols, and in particular maltitol, mannitol, xylitol, erythritol, sorbitol, glycerol, glycerol and sorbitol being the preferred polyols. Preferably, this polyol is crystallized or else is in the form of a powder.

Thus, in particular, the object of the invention is an emulsifying composition, in particular for cosmetic use and capable of obtaining an oil-in-water (O/W) emulsion that comprises, or which preferably consists of:
1) 40% to 95% by weight, with respect to the total weight of the composition, of at least one cyclodextrin in the form of solid particles, said particles having a volumetric average particle size d(4.3), measured by laser granulometry, of between 2 and 20 µm, preferably between 3 and 12 µm, and more preferably between 4 and 8 µm,
2) 5% to 40% by weight, with respect to the total weight of the composition of at least one emulsifier of natural origin selected from water-in-oil-type (W/O) emulsifiers, having a HLB of less than 8, and more preferably having a HLB of less than or equal to 7,
3) and 0% to 40% by weight, with respect to the total weight of the composition of at least one polyol.

Preferably, this emulsifying composition according to the present invention comprises, or preferably consists of:
1) 45% to 85% by weight, with respect to the total weight of the composition of at least one cyclodextrin in the form of solid particles, said particles having a volumetric average particle size d(4.3), measured by laser granulometry, of between 2 and 20 µm, preferably between 3 and 12 µm, and more preferably between 4 and 8 µm,
2) 5% to 30% by weight, with respect to the total weight of the composition of at least one emulsifier of natural origin selected from water-in-oil-type emulsifiers, having a HLB of less than 8, and more preferably having a HLB of less than or equal to 7,
3) and 10% to 40% by weight, with respect to the total weight of the composition of at least one polyol.

Preferably, this composition according to the present invention comprises, or preferably consists of:
1) 40% to 80% by weight, with respect to the total weight of the composition of at least one cyclodextrin in the form of solid particles, said particles having a volumetric average particle size d(4.3), measured by laser granulometry, of between 2 and 20 µm, preferably between 3 and 12 µm, and more preferably between 4 and 8 µm,
2) 10% to 20% by weight, with respect to the total weight of the composition of at least one emulsifier of natural origin selected from water-in-oil-type emulsifiers, having a HLB of less than 8, and more preferably having a HLB of less than or equal to 7,
3) and 10% to 30% by weight, with respect to the total weight of the composition of at least one polyol.

In the three embodiments of the emulsifying composition mentioned above, it is preferred that the water-in-oil emulsifier with a HLB of less than 8 be a non-ethoxylated polyol fatty esters with an HLB of less than 8.

Emulsion, Preferably of the Pickering Type, Implementing the Emulsifying Composition The emulsifying composition according to the invention enable emulsions to be performed, in particular of the Pickering type, advantageously being able to be stabilized by the organic particles compatible with the skin or the hair. The so-called "Pickering" emulsions are obtained by replacing the surfactants with emulsifying systems composed of solid micro-particles in association with fatty products.

The emulsifying composition according to the invention can comprise in a complementary manner other products suitable for forming or stabilizing Pickering emulsions such as silicas and starch octenylsuccinates in the form of calcium or aluminum salts.

Thus another object of the present invention relates to a preferably Pickering oil-in-water-type (O/W) emulsion, in particular for cosmetic use, characterized in that it contains at least one cyclodextrin in the form of solid particles, said particles having a volumetric average particle size d(4.3), measured by laser granulometry, of between 2 and 20 µm, preferably between 3 and 12 µm, and more preferably between 4 and 8 µm, and at least one emulsion of natural origin in a emulsifier/cyclodextrin ratio (weight/weight) of between 0.01:1 and 1:1, preferably of between 0.15:1 and 0.30:1. Said emulsifier of natural origin has a HLB of less than 8, preferably of less than or equal to 7.

The emulsion, in particular Pickering, implementing the emulsifying composition according to the invention, comprises an aqueous phase further composed of water.

According to an embodiment classed as "water rich", the water content in the emulsion is of between 50% and 95%, preferably between 60% and 92%, most preferably between 65% and 90%, by weight with respect to the total weight of the emulsion. The emulsion according to this embodiment is ready for use, and can thus be used without the user adding additional water.

According to an embodiment classed as "water poor", the water content in the emulsion is of between 2% and 50%, preferably between 5% and 35%, most preferably between 10% and 40%, by weight with respect to the total weight of the emulsion. The emulsion according to this embodiment presents the advantage of reducing the total mass of the containers such as flasks, bottles or pots, by reducing the water mass present in the emulsion. This reduces the cost of transport and the amount of exhaust gases released by such transport. It may be the case that the user must add water at the time of use in order to ensure a correct use of this embodiment of the emulsion.

The emulsion, in particular O/W Pickering, implementing the emulsifying composition according to the invention can further comprise a fatty phase that can be liquid at room temperature (25° C.), such as e.g. vegetable oils, or solid such as in the case of waxes. This liquid fatty phase can be of mineral, animal, vegetable or synthetic origin and be composed of hydrocarbonated oils, or optionally silicone oils. Hydrocarbonated oil is understood as an oil essentially formed, or constituted by, carbon atoms and hydrogen and optionally oxygen and nitrogen atoms, being able to contain alcohol, ester, ether, carboxylic acid, amine and/or amide groups. The oil content of the final O/W emulsion is preferably of between 10 and 65% by weight, and preferably of the order of 20 to 55% by weight.

Preferably, the emulsion implementing the emulsifying composition according to the invention may comprise one or more oils, preferably at least one non-volatile liquid oil. Non-volatile liquid oil is understood as an oil susceptible to remaining on the skin at room temperature, at atmospheric pressure for at least one hour.

The liquid fatty phase advantageously comprises one or more non-volatile oils that procure an emollient effect on the skin. These can include fatty acids such as cetearyl isononoate, isotridecyl isononoate, isostearyl isostearate, isopropyl isostearate, isopropyl myristate, isopropyl palmitate, butyl stearate, hexyl laurate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl maleate, tracetin, tricprin, caprylic/capric acid triglyceride, glycerin triisostearate, tocopheryl acetate, higher fatty acids such as myristic acid, palmitic acid, stearic acid, behenic acid, oleic acid, linoleic acid, linolenic acid or isostearic acid, higher fatty alcohols such as oleic alcohol, vegetable oils such as avocado oil, camellia oil, hazelnut oil, tsubaki oil, cashew nut oil, argan oil, soybean oil, grape seed oil, sesame oil, "mals" oil, wheat germ oil, canola oil, sunflower oil, cotton oil, jojoba oil, peanut oil, olive oil and mixtures thereof, vegetable butters such as shea butter, camellia butter.

These oils can be hydrocarbonated or siliconized-type oils such as paraffin oil, squalane oil, petrolatum, dimethyl siloxanes and mixtures thereof.

The liquid fatty phase can also optionally comprise volatile oils. Volatile oil is understood as an oil susceptible to evaporating from the skin, in less than one hour at room temperature and atmospheric pressure. Volatile oils can be for example selected from silicone oils or short fatty acid triglycerides to reduce the greasy feel.

Preferably, the emulsion-type composition, in particular O/W Pickering, implementing the emulsifying composition according to the invention only contains oils of renewable origin and in particular oils or butters of vegetable origin, preferably refined. These oils and butters perfectly complement the emulsifying system implemented in the emulsifying composition object of the invention in the sense that they enable very stable emulsions to be obtained, with high whiteness and an easily adjustable viscosity. The emulsifying composition according to the invention advantageously enables oil-in-water emulsions to be prepared at high oil content. This type of O/W-type emulsions rich in oil is normally difficult to obtain in a stable form over time with conventional emulsifiers. The oil content of the O/W emulsion implementing the emulsifying composition according to the invention is preferably of between 10 and 65% by weight, and preferably to the order of 20 to 55% by weight with respect to the total weight of the emulsion. The vegetable oils or oils of plant origin such as e.g. sunflower oil and isopropyl palmitate in particular enable stable emulsions to be obtained, not giving rise to creaming or phase separation.

The emulsion implementing the emulsifying composition according to the invention can further comprise a rheological agent in particular such as a thickening agent of the aqueous phase, or a gelling agent or a suspending agent, such as e.g. gums derived from plants such as gum arabic, konjac gum, guar gum or derivatives thereof; gums extracted from algae such as alginates or carrageenan; gums derived from microbial fermentation such as xanthans, mannan, scleroglucans or derivatives thereof; cellulose and derivatives thereof such as carboxymethyl cellulose or hydroxyethyl cellulose; starch and its derivatives in particular such as modified starches, in particular acetylated, carboxymethylated, octenylsuccinates or hydroxypropylated, synthetic polymers such as polyacrylic acid or carbomers.

Preferably, the emulsion implementing the emulsifying composition according to the invention comprises a rheological agent selected from natural polysaccharides derived from plants or fermentation, optionally modified. Xanthans and derivatives thereof in particular enable oil-in-water emulsions to be obtained with very fine droplet sizes, even used at a content of less than 1% by weight, with respect to the total weight of the emulsion.

The emulsions implementing the emulsifying composition according to the invention are preferably present in the form of a fatty phase dispersed in an aqueous phase, said dispersed fatty phase being presented in the form of droplets with an average size of less than or equal to 30 µm, preferably of less than or equal to 10 µm.

A small droplet size increases the stability of the emulsion by reducing the flocculation rate of the emulsion, and thus the phase separation rate. The average droplet size depends on a large number of parameters and, thus, constitutes a characteristic that should be controlled and is not intrinsic to the formulation of the emulsifying composition.

The average droplet size can be measured by means of a LEICA DMLS optical microscope at ×10 magnification, followed by a count and calculation of an average over at least ten droplets.

The emulsion implementing the emulsifying composition according to the invention can further comprise a preservative selected from benzyl alcohol, dehydroacetic acid and mixtures thereof.

The emulsion implementing the emulsifying composition according to the invention preferably presents a viscosity greater than 3000 mPa·s at 25° C., preferably greater than 5000 mPa·s at 25° C. The viscosity is measured using a Brookfield DV-II+Pro viscometer in rotation at a speed of 20 rotations per minute in contact with the product sample. The resistance of the product to this rotational movement is registered during one minute and converted into "mPascal second", commonly denoted as mPa·s. For each sample, the viscosity is measured three times and the arithmetic mean of three values is retained.

In order to characterize the sensory properties of emulsifying compositions according to the invention, sensory descriptors and a corresponding 5-step sensory evaluation protocol are used. These 5 steps correspond to the different phases of application of a treatment product: appearance, handling, application, spreading after 1 minute, and spreading after 2 minutes. During these 5 phases, several sensory descriptors are evaluated by a panel of ten evaluators, in order to compare an emulsion according to the invention to an emulsion according to the patent application FR1762841 filed by the present applicant. The emulsions according to the invention are distinguished from emulsions according to the patent FR1762841 in the sensory smoothness, greasiness, softness, squeakiness, penetrability and pilling properties. The emulsions according to the invention provide a texture that is easier to spread and that penetrates quicker, as well as a greasier feel, but still smoother, softer, and less squeaky. In addition, there is less pilling, or even no pilling depending on the skins.

Moreover, the emulsifying composition according to the invention enables the easy realization of oil-in-water O/W emulsions that are both very stable and very fine, with buildable textures, having a fresh, silky and non-greasy touch, even for high contents in dispersed fatty phase. It is thus possible to obtain emulsions having a good emollient effect on the skin as well as a good moisturizing effect of the upper layers of the epidermis.

This emulsifying composition in particular enables the easy realization of very fine O/W emulsions with varied textures, very compatible with the skin and also having a dry, fresh and silky touch, and this even with a high content in fatty phase in the emulsion.

Method for Manufacturing a Liquid Emulsion Implementing the Emulsifying Composition Another object of the present invention consists of a method for manufacturing a liquid oil-in-water emulsion, preferably Pickering, in particular for cosmetic use, comprising the following steps:

a) dispersing, in an aqueous phase, an emulsifying composition comprising at least one cyclodextrin in the form of solid particles, said particles having a volumetric average particle size d(4.3), measured by laser granulometry, of between 2 and 20 µm, preferably between 3 and 12 µm, and more preferably between 4 and 8 µm, and at least one emulsifier of natural origin selected from water-in-oil-type emulsifiers, having a HLB of less than 8, most preferably of less than or equal to 7, in an emulsifier/cyclodextrin ratio of between 0.01:1 and 1:1, preferably between 0.15:1 and 0.30:1, b) adding a fatty phase to the mixture obtained in step a) in an amount of between 10 and 65% by weight, with respect to the total weight of the composition, under stirring to enable the dispersion of the fatty phase in the aqueous phase in the form of droplets with an average size of less than 30 µm, preferably of less than or equal to 10 µm.

According to a variant, the method according to the invention of making a liquid oil-in-water emulsion, preferably of the Pickering type, in particular for cosmetic use, comprises the following steps:

a) dispersing, in a fatty phase, an emulsifying composition comprising at least one cyclodextrin in the form of solid particles, said particles having a volumetric average particle size d(4.3), measured by laser granulometry, of between 2 and 20 µm, preferably between 3 and 12 µm, and more preferably between 4 and 8 µm, and at least one emulsifier of natural origin selected from water-in-oil-type emulsifiers, having a HLB of less than 8, and more preferably a non-ethoxylated polyol fatty esters with a HLB of less than 8, in an emulsifier/cyclodextrin ratio of between 0.01:1 and 1:1, preferably between 0.15:1 and 0.30:1, the fatty phase preferably representing between 10 and 65% by weight, and preferably between 20 and 55% by weight, with respect to the final weight of the emulsion, b) and adding the mixture obtained in step a) to an aqueous phase under stirring to enable the dispersion of the fatty phase in the aqueous phase in the form of droplets with an average size of less than or equal to 30 µm, preferably of less than or equal to 10 µm.

Use

Lastly, an object of the invention is also the use:

of at least one cyclodextrin in the form of solid particles having a volumetric average particle size d(4.3) measured by laser granulometry, of between 2 and 20 µm, preferably between 3 and 12 µm, and more preferably between 4 and 8 µm, and of at least one emulsifier of natural origin selected from water-in-oil-type emulsifiers, having a hydrophilic-lipophilic balance of less than 8, most preferably of less than or equal to 7, in a liquid emulsion for cosmetic use to provide said emulsion with a softer and smoother feel, make said emulsion easier to spread, and reduce or eliminate pilling.

EXAMPLES

The invention will be better understood with the aid of the non-limiting exemplary embodiments described hereinafter.

Example 1: Emulsion

An oil-in-water emulsion embodied according to the invention was compared with a so-called "reference" oil-in-water emulsion, realized outside of the invention, both prepared according to the composition of Table 1.

TABLE 1

| Composition of the emulsion | |
|---|---|
| Component/INCI name | Mass % |
| Sunflower oil/Helianthus annuus seed oil | 30 |
| Beta-cyclodextrin/Cyclodextrin | 2.5 |
| Sorbitol (powdered) | 1 |
| Polyglyceryl-3 diisostearate | 0.5 |
| Demineralized water/Aqua | 64.3 |
| Xanthan gum/Xanthan gum | 0.7 |
| Preservative | 1 |

The reference emulsion is obtained by using a beta-cyclodextrin marketed under the name "Beauté by Roquette® CD102" by the applicant. The emulsion according to the invention is obtained by using this same beta-cyclodextrin previously dry ground to have a volumetric average size d(4.3) of less than 20 µm; the beta-cyclodextrin thus obtained is qualified as "ultra-fine". The granulometric characteristics of these two beta-cyclodextrins are presented in Table 2.

TABLE 2

| granulometric characteristics of the beta-cyclodextrins | | |
|---|---|---|
| | Beta-cyclodextrin "Beauté by Roquette ® CD102" (reference) | Beta-cyclodextrin according to the invention, so-called "ultra-fine" |
| d(4.3) (µm) | 94.83 | 11.43 |
| d10 (µm) | 21.81 | 2.378 |
| d50 (µm) | 85.81 | 9.716 |

TABLE 2-continued granulometric characteristics of the beta-cyclodextrins

| | Beta-cyclodextrin "Beauté by Roquette ® CD102" (reference) | Beta-cyclodextrin according to the invention, so-called "ultra-fine" |
|---|---|---|
| d90 (μm) | 182.2 | 22.85 |
| CV | 64.7% | 72.3% |

The protocol for preparing the emulsions is the following. First a thickening agent is dispersed, in this case xanthan gum, in water at 40° C. under stirring with deflocculation blades at 500 revolutions per minute. Separately, the beta-cyclodextrin is mixed with the sorbitol and the polyglyceryl-3 diisostearate. This mixture is then added into the water containing the thickening agent, under stirring at 1000 revolutions per minute, in order to obtain an aqueous phase.

The amount of beta-cyclodextrin is set at 2.5% by weight of the emulsion for the two emulsions.

The sunflower oil constitutes the oily phase, it is heated to 40° C.

The oily phase is thus emulsified in the aqueous phase at 40° C. under stirring at 3000 revolutions per minute for 20 minutes.

It is left to cool and when at room temperature (20° C.), a phenoxyethanol-based preservative is then added.

For each of the emulsions, physical and chemical characteristics are measured, namely the viscosity and the average size of the droplets, and sensory characteristics are measured, namely fluidity, slipperiness, spreadability, greasiness, softness, squeakiness, penetrability, smoothness and pilling.

Viscosity is measured using a Brookfield DV-II+Pro viscometer. A fixed-size moving part (SP2 to SP7 moving parts used according to the viscosity levels in accordance with apparatus instructions) is rotated at a speed of 20 revolutions per minute in contact with the product sample. The resistance of the product to this rotational movement is registered during one minute and converted into millipascal-second. For each sample, the viscosity is measured three times and the arithmetic mean of three values is retained.

The average size of the droplets is determined by carrying out the arithmetic mean of the droplet sizes measured with an optical microscope at ×10 magnification, on a representative number of droplets, typically at least 10 droplets. The microscope used is a LEICA DMLS.

The sensory characteristics are evaluated by a panel of ten people who are experts in analyzing the texture of cosmetic products.

When spreading the product, two descriptors are evaluated. The examination of the product is done under the lamp, after having deposited 50 to 100 μL of the product under examination on the hand, while it is spread for 10 turns.

The smoothness descriptor is evaluated between the 2nd and 5th turn. The fingers slide well over the skin. The product is perceived as a powdery substance on the skin.

Spreading is evaluated by examining the product after having placed 50-100 μl of the product on the hand, while it is spread for 10 turns, under a lamp. Spreading is highest when there is little resistance to movement between the 5th and the 10th turn on the hand.

The following descriptors are evaluated after 10 turns are carried out.

For the following two descriptors, the examination is carried out under a lamp, on the skin, 1 minute after spreading 50 to 100 μl of the product.

The softness descriptor is evaluated by sliding over the skin: a dry and slippery sensation is felt.

The squeakiness descriptor is evaluated by rubbing the thumb with the index finger, resistance is felt, and a squeaky sound is heard.

For the following two descriptors, the examination is carried out under the lamp, on the skin, 2 minutes after spreading 50 to 100 μl of the product.

The penetration descriptor of the product is evaluated by sliding over the skin. A panel of evaluators then evaluates the amount of product residue recovered.

The pilling is evaluated by carrying out a mechanical rubbing action on the skin, the product leads to the formation of pills.

TABLE 3 improved sensory perceptions with respect to the reference emulsion

| Sensory perception | Emulsion according to the invention, with "ultra-fine" beta-cyclodextrin, with respect to the emulsion with Beauté by Roquette ® CD102 |
|---|---|
| Smooth | Smoother |
| Spread | Easier |
| Softness | Softer feel |
| Squeaky | Notably less squeaky |
| Penetrating | Faster penetration |
| Pilling | No pilling or less pilling |

The criteria for improved sensory properties in the emulsion according to the invention are: fluidity, smoothness, spreadability, greasy, softness, squeaky, penetrability, pilling.

Example 2: Sunscreen

The sensory profile of a sunscreen formulation prepared with a beta-cyclodextrin with an average diameter of 200 μm (Beauté by Roquette® CD102 of example 1) or with a beta-cyclodextrin with a volumetric average particle size of 11.43 μm (ultra-fine beta-cyclodextrin of example 1), according to the operating mode hereinafter.

First, phase A1 is prepared according to the composition of Table 4: the Sunsphere powder is dispersed in the water and the Cetiol C5, it is then heated to 55° C. under stirring at 2000 rpm with a rotor-stator for 15 minutes.

TABLE 4

Composition of phase A1

| Phase | Trade name | Supplier | INCI name | % m of the total |
|---|---|---|---|---|
| A1 | Demineralized water | Cooper | Aqua | 36.44 |
| | EDETA BD | AMI Chimie | Disodium EDTA | 0.10 |
| | Sunsphere powder | Dow (Univar) | Styrene/acrylate copolymer | 5.00 |
| | Cetiol C5 | AMI Chimie | Coco-caprylate | 1.00 |

Separately, phase A2 is prepared by weighing all the ingredients in a cup, then it is added to phase A1 under stirring with rotor-stator at 2000 rpm for 15 minutes. Phase A1+A2 is stored at 70° C. under stirring.

TABLE 5 composition of phase A2

| Phase | Trade name | Supplier | INCI name | % m of the total |
|---|---|---|---|---|
| A2 | Sepinov WEO | Seppic | Hydroxymethyl Acrylate/Sodium Acryloyldimethyl Taurate Copolymer | 0.20 |
| | Microcare PHC | Thor | Glycerin & Chlorphenesin & Phenoxyethanol | 1.00 |
| | Xanthan gum | Interchimie | Xanthan gum | 0.30 |
| | Glycérine codex | Cooper | Glycerin | 3.00 |
| | Romol AFSK | Saci cfpa | Potassium cetyl phosphate | 0.30 |

Phase B1 is then prepared by heating to 70° C. under magnetic stirring for 10 minutes according to the composition of Table 6.

TABLE 6 composition of phase B1

| Phase | Trade name | Supplier | INCI name | % m of the total |
|---|---|---|---|---|
| B1 | Cetiol C5 | AMI Chimie | Coco-caprylate | 2.00 |
| | Cocoate BG | Gattefossé | Butylene glycol cocoate | 2.00 |
| | Parsol 1789 | IES Ingrédients | Butyl MethoxyDibenzoylMethan | 5.00 |
| | Parsol EHS | IES Ingrédients | Ethylhexyl Salicylate | 5.00 |
| | Parsol MCX | IES Ingrédients | Ethylhexyl Methoxycinnamate | 7.50 |
| | Parsol HMS | IES Ingrédients | Homosalate | 9.00 |
| | Solastay S1 | Azelis | Ethylhexyl methoxycrylene | 3.00 |
| | Hallbrite BHB | Azelis | Butyl Octyl Salycilate | 4.00 |
| | Tinogard TL | AMI Chimie | Benzotriazolyl Dodecyl P-Cresol | 1.00 |
| | Covanol Red ON 3780 | Sensient | Iron oxides (CI77491) & Octyldodecanol & Stearic acid & Magnesium hydroxide & Aluminium hydroxide & Sorbitan oleate | 0.12 |
| | Covanol Yellow ON 1782 | Sensient | Iron oxides (CI77492) & Octyldodecanol & Stearic acid & Magnesium hydroxide & Aluminium hydroxide & Sorbitan oleate | 0.53 |
| | Oleic sunflower oil | Oléon | Helianthus annuus seed oil | 3.00 |

Storing phase B1 at 70° C. under stirring, phase B2 is added, prepared separately and constituted according to the composition of Table 7, and it is kept under stirring for 10 minutes, after which the phase B1+B2 is emulsified in phase A.

TABLE 7 composition of phase B2

| Phase | Trade name | Supplier | INCI name | % m of the total |
|---|---|---|---|---|
| B2 | Beauté by Roquette ® CD102 | Roquette Frères | Cyclodextrin | 2.5 |
| | Plurol | Gattefossé | Polyglyceryl 3-diisostearate | 0.5 |

TABLE 7-continued composition of phase B2

| Phase | Trade name | Supplier | INCI name | % m of the total |
|---|---|---|---|---|
| | Neosorb | Roquette Frères | Sorbitol | 1 |

To emulsify the phase B1+B2 in phase A, the entirety of phase B1+B2 is poured into phase A at 55° C. under stirring with rotor-stator at 2500 rpm, which is then maintained for 5 minutes at 55° C., and for 10 minutes under cold water bath. The speed is reduced to 1200 rpm and stirring continues until the emulsion is at room temperature under cold water bath.

Phase C is then added, it is then colored with phase D.

TABLE 8 composition of phases C and D

| Phase | Trade name | Supplier | INCI name | % m of the total |
|---|---|---|---|---|
| C | Plouf RL G 113 23705 | Robertet | Perfume | 0.50 |
| D | Covarine white WN 9787 | Sensient | CI 77891 (and) Glycerin (and) Xanthan Gum (and) Sodium Citrate (and) Aqua | 4.00 |
| | Covarine black WN 9798 | Sensient | CI 77499 & Glycerin & Xanthan gum & Sodium citrate & Aqua | 0.01 |

A tinted and perfumed cream is thus obtained. When it is applied on the skin, the cream pills, it is comfortable but a squeaky effect is noted when it is spread.

A sunscreen is then prepared according to the previous protocol by substituting "Beauté by Roquette® CD102" for the "ultra-fine" beta-cyclodextrin of example 1. The cream is applied on the skin: there is no pilling, the cream is more comfortable. A slight squeaky effect persists at the end of the penetration of the cream, but it is significantly less present than with the reference formulation comprising the beta-cyclodextrin "Beauté by Roquette® CD102".

The invention claimed is:

1. An emulsifying composition, capable of obtaining a liquid oil-in-water-type emulsion comprising:
   a) at least one cyclodextrin in the form of solid particles, said particles having a volumetric average particle size d(4.3), measured by laser granulometry, of between 2 and 20 μm,
   b) and at least one emulsifier of natural origin selected from water-in-oil-type emulsifiers, having a hydrophilic-lipophilic balance of less than 8.

2. The emulsifying composition according to claim 1, wherein the cyclodextrin particles have a volumetric particle size distribution, measured by laser diffraction granulometry, the characteristic diameters d(10), d(50) and d(90) of which are such that:
   a) The diameter d(10) is of less than or equal to 5.0 μm, and/or
   b) the diameter d(50) is of less than or equal to 15.0 μm, and/or
   c) the diameter d(90) is of less than or equal to 30.0 μm.

3. The emulsifying composition according to claim 1, wherein the solid cyclodextrin particles have a volumetric particle size distribution, measured by laser diffraction granulometry, having a coefficient of variation of less than or equal to 100%.

4. The emulsifying composition according to claim 1 wherein the water-in-oil emulsifier of natural origin is selected from emulsifiers having a hydrophilic-lipophilic balance (HLB) of between 1.5 and 6.0.

5. The emulsifying composition according to claim 1, wherein the average HLB of the overall emulsifying system of said composition is of less than 8.

6. The emulsifying composition according to claim 1, wherein the emulsifier of natural origin is present in the emulsifying composition in an emulsifier/cyclodextrin ratio of between 0.01:1 and 1:1.

7. The emulsifying composition according to claim 1, wherein said cyclodextrin is selected from the alpha-, beta- and gamma-cyclodextrins.

8. The emulsifying composition according to claim 1, wherein the emulsifier of natural origin is a water-in-oil emulsifier selected from non-ethoxylated polyol fatty esters.

9. The emulsifying composition according to claim 1, wherein the water-in-oil emulsifier of natural origin is selected from non-ethoxylated polyol fatty esters obtained from fatty acids or by transesterification from oil or oil mixtures.

10. The emulsifying composition according to claim 1, comprising:
   1) 40% to 95% of at least one cyclodextrin in the form of solid particles, said particles having a volumetric average particle size d(4.3), measured by laser granulometry, of between 2 and 20 μm,
   2) 5% to 40% of at least one emulsifier of natural origin selected from water-in-oil-type emulsifiers, having a hydrophilic-lipophilic balance of less than 8, and
   3) 0% to 40% of at least one polyol.

11. The composition according to claim 1, having a viscosity greater than 3,000 mPa·s at 25° C.

12. The emulsifying composition according to claim 1, wherein-said cyclodextrin is a native beta-cyclodextrin.

13. The emulsifying composition according to claim 1, wherein:
   a) the diameter d(10) is of less than or equal to 2.5 μm, and/or
   b) the diameter d(50) is of less than or equal to 10.0 μm, and/or
   c) the diameter d(90) is of less than or equal to 25.0 μm.

14. The emulsifying composition according to claim 1, wherein the emulsifier of natural origin is present in the emulsifying composition in an emulsifier/cyclodextrin ratio of between 0.15:1 and 0.30:1.

15. An oil-in-water Pickering liquid emulsion, wherein said liquid emulsion comprises at least one cyclodextrin in the form of solid particles, said particles having a volumetric average particle size d(4.3) of between 2 and 20 μm, and at least one emulsifier of natural origin selected from water-in-oil emulsifiers, having a hydrophilic-lipophilic balance of less than 8, in an emulsifier/cyclodextrin ratio of between 0.01:1 and 1:1.

16. The emulsion according to claim 15, wherein said emulsion-presents itself in the form of a fatty phase dispersed in an aqueous phase, said dispersed fatty phase presenting itself in the form of droplets with an average size in number of less than 30 μm.

17. A method for manufacturing a liquid emulsion, comprising the following steps:
   a) dispersing, in an aqueous phase, an emulsifying composition comprising at least one cyclodextrin in the form of solid particles, said particles having a volumetric average particle size d(4.3) measured by laser granulometry, of between 2 and 20 μm, and at least one emulsifier of natural origin selected from water-in-oil-type emulsifiers, having a hydrophilic-lipophilic balance of less than 8, in an emulsifier/cyclodextrin ratio of between 0.01:1 and 1:1,
   b) adding a fatty phase to the mixture obtained in step a) in an amount of between 10 and 65% by weight, with respect to the total weight of the composition, under stirring to enable the dispersion of the fatty phase in the aqueous phase in the form of droplets with an average size of less than or equal to 30 μm.

18. A method for providing an emulsion with a softer and smoother feel, and easier to spread, and to reduce or eliminate pilling by combining at least one cyclodextrin in the form of solid particles having a volumetric average particle size d(4.3) measured by laser granulometry, of between 2 and 20 μm, and of at least one emulsifier of natural origin selected from water-in-oil-type emulsifiers, having a hydrophilic-lipophilic balance of less than 8.

19. The emulsifying composition according to claim 1 or the liquid emulsion according to claim 11 or the method according to claim 17 or 18, wherein the volumetric average particle size d(4.3), measured by laser granulometry, is of between 3 and 12 μm.

20. The emulsifying composition according to claim 1 or the liquid emulsion according to claim 15 or the method according to claim 17 or 18 wherein the hydrophilic-lipophilic balance is less than or equal to 7.

* * * * *